US009044604B2

(12) United States Patent
Dirauf et al.

(10) Patent No.: US 9,044,604 B2
(45) Date of Patent: Jun. 2, 2015

(54) RADIOTHERAPY SYSTEM

(75) Inventors: Franz Dirauf, Ebensfeld (DE); Franz Fadler, Hetzles (DE)

(73) Assignee: Siemens Aktiengesellschaft, München (DE)

( * ) Notice: Subject to any disclaimer, the term of this patent is extended or adjusted under 35 U.S.C. 154(b) by 781 days.

(21) Appl. No.: 13/312,687

(22) Filed: Dec. 6, 2011

(65) Prior Publication Data

US 2012/0307973 A1 Dec. 6, 2012

(30) Foreign Application Priority Data

Dec. 7, 2010 (DE) .................... 10 2010 062 533

(51) Int. Cl.
*A61N 5/10* (2006.01)
*A61B 6/03* (2006.01)
*A61B 6/00* (2006.01)

(52) U.S. Cl.
CPC ............. *A61N 5/1049* (2013.01); *A61B 6/032* (2013.01); *A61B 6/4014* (2013.01); *A61B 6/4452* (2013.01); *A61N 2005/1061* (2013.01)

(58) Field of Classification Search
CPC .............. A61N 5/1049; A61N 2005/1061; A61B 6/032; A61B 6/4014; A61B 6/4452
USPC ................................. 378/4, 62, 65
See application file for complete search history.

(56) References Cited

U.S. PATENT DOCUMENTS

| 6,155,713 | A | 12/2000 | Watanabe |
| 6,865,254 | B2 | 3/2005 | Näfstadius |
| 7,477,722 | B2 | 1/2009 | Carrano et al. |
| 2003/0048868 | A1* | 3/2003 | Bailey et al. .................... 378/65 |
| 2004/0005027 | A1 | 1/2004 | Nafstadius |
| 2009/0003523 | A1* | 1/2009 | Raanes et al. ................... 378/65 |
| 2010/0067660 | A1 | 3/2010 | Maurer, Jr. et al. |

FOREIGN PATENT DOCUMENTS

| CN | 101238351 | 8/2008 |
| DE | 10 2009 049 074 A1 | 4/2011 |
| EP | 2 305 350 A1 | 4/2011 |

OTHER PUBLICATIONS

German Office Action dated Nov. 24, 2011 for corresponding German Patent Application No. DE 10 2010 062 533.7 with English translation.
Chinese Office Action cited in CN201110404004.2, mailed Sep. 18, 2014.

* cited by examiner

*Primary Examiner* — Irakli Kiknadze
(74) *Attorney, Agent, or Firm* — Lempia Summerfield Katz LLC

(57) ABSTRACT

The present embodiments relate to a radiotherapy system including a radiotherapy module and at least one X-ray imaging module. The radiotherapy module and the X-ray imaging module may be moved independently of each other.

12 Claims, 8 Drawing Sheets

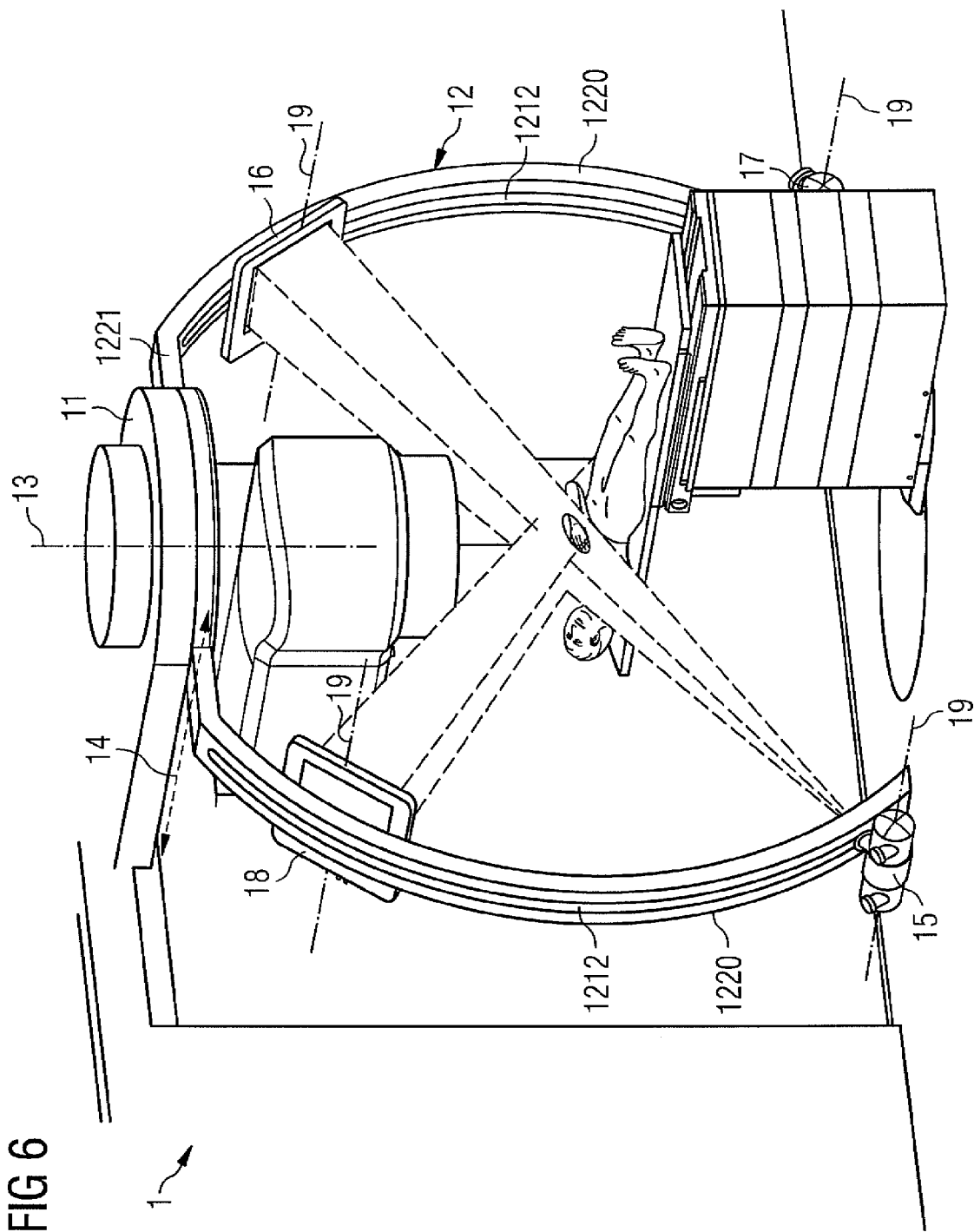

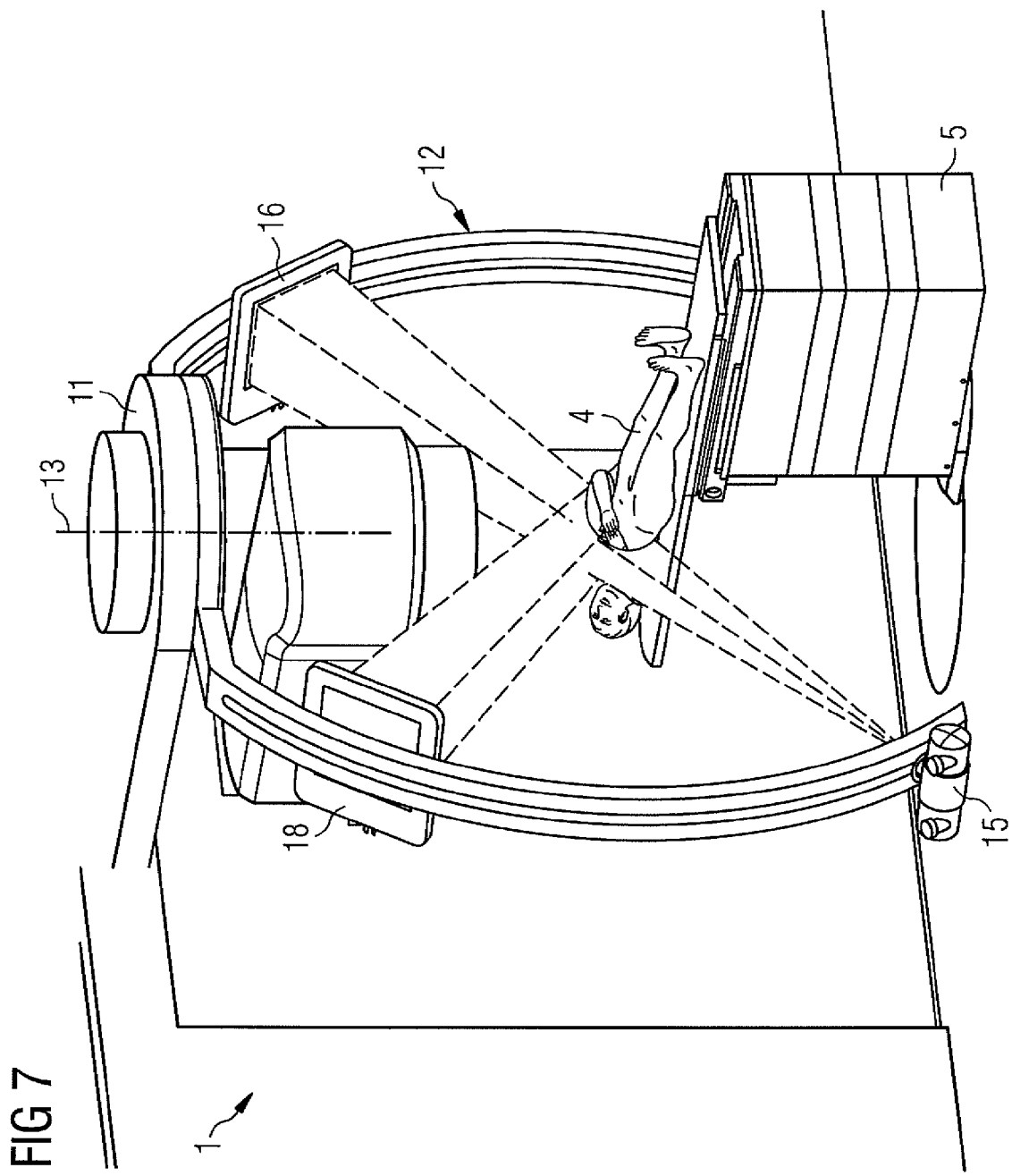

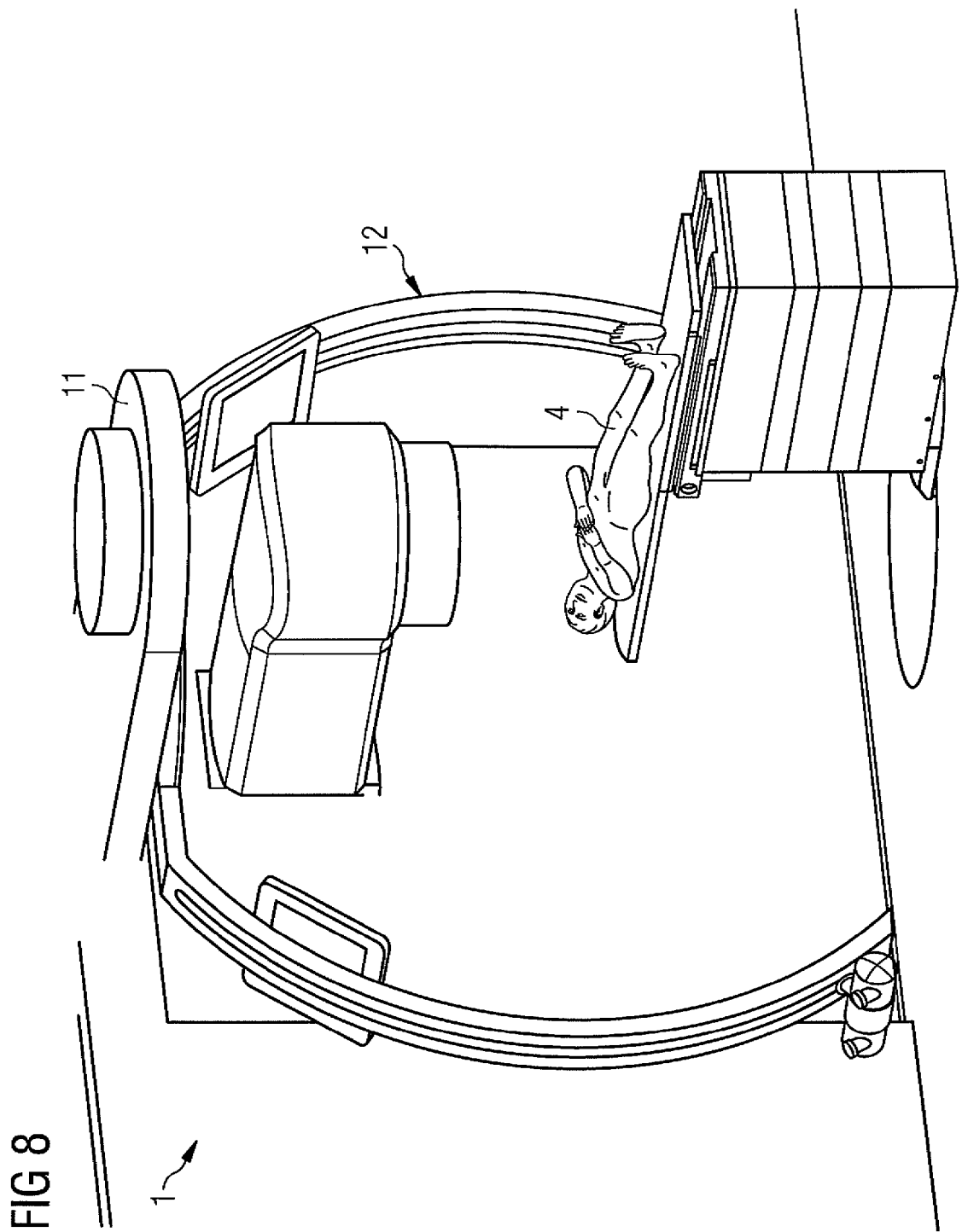

RADIOTHERAPY SYSTEM

This application claims the benefit of DE 10 2010 062 533.7, filed on Dec. 7, 2010.

BACKGROUND

The present embodiments relate to a radiotherapy system including a therapeutic radiotherapy module and at least one diagnostic X-ray imaging module.

The use of radiation to destroy diseased tissue is a common method in therapeutic medicine. Systems that use high-energy, electromagnetic radiation (e.g., X-rays, gamma radiation), or particle radiation (e.g., electrons, protons, and/or carbon ions) are used for this purpose. The radiation used in radiotherapy may, for example, be in the megavolt (MV) energy range. During the course of a radiotherapy session, the patient is precisely positioned to provide that a body region to be irradiated (e.g., a tumor to be irradiated) is exposed to a sufficiently high radiation dose, but at the same time, the patient's healthy tissue is damaged as little as possible. A localization of a body region of the patient to be irradiated is conventionally performed at regular intervals during the treatment for the purpose of positioning. This may take place with imaging X-ray methods using radiation in the kilovolt (kV) energy range (e.g., using computed tomography). To avoid incorrect positioning of the patient, an examination of this kind may be carried out directly in the irradiation position.

During radiation treatments using radiation from different directions, the beam strikes the tumor for each of the directions. The beams intersect at a point that lies in the region of the tissue to be irradiated. The point may be an isocenter and is an intersection point of the beams corresponding with different irradiation positions.

Published document DE 10 2009 049 074 A1 discloses a radiotherapy system having a therapeutic radiation source and two diagnostic X-ray imaging modules each with an X-ray source and an X-ray detector. FIG. 1 shows a radiotherapy system 1 including a rotatable gantry 2 that is constructed with a cylindrical opening 3, in which a patient 4 undergoing radiotherapy may be at least partially positioned. The patient 4 is positioned by way of a couch 5 in such a way that the tumor of the patient 4 is located in the isocenter of the radiotherapy system 1. A projecting arm 6 is arranged on the gantry 2. A radiation source (not shown in FIG. 1) for a therapeutic treatment beam 7 that strikes the patient 4 during treatment, and a lamella collimator are at least partially located in the projecting arm 6. Also provided on the projecting arm 6 is a holding ring 8 that is concentrically oriented with respect to the isocenter of the radiotherapy system 1. A plane of the holding ring 8 is located in a plane of rotation of the rotatable gantry 2. Two X-ray sources 9 and two X-ray detectors 10 are arranged on the holding ring 8 so as to be movable along the holding ring 8 independently of each other. The position, shown in FIG. 1, of the X-ray imaging module with mutually opposing X-ray sources 9 and X-ray detectors 10 is used to produce an X-ray image or a sequence of X-ray images of the patient 4. When the gantry 2 is rotated, a direction of the therapeutic treatment beam 7, from which the therapeutic treatment beam 7 strikes the patient 4, changes. As the gantry 2 is rotated, the holding ring 8 rotates at the same time. The position of the X-ray sources 9 and the X-ray detectors 10 rotates as well. Since the X-ray sources 9 and the X-ray detectors 10 are arranged on the holding ring 8 so as to be movable independently of each other, the angle may be flexibly adjusted for diagnostic X-ray imaging. The X-ray imaging module and the mobility of the associated X-ray imaging components are tied to the specific embodiment of the projecting arm 6 of the radiotherapy system.

SUMMARY AND DESCRIPTION

The present embodiments may obviate one or more of the drawbacks or limitations in the related art. For example, a radiotherapy system having at least one X-ray imaging module is provided.

In one embodiment, a radiotherapy system having a radiotherapy module and at least one X-ray imaging module is provided. The radiotherapy module and the at least one X-ray imaging module may be moved independently of each other. As a result, maximized flexibility when positioning the diagnostic X-ray imaging module during therapeutic radiotherapy is advantageously achieved.

In one embodiment, the X-ray imaging module may include an X-ray source and an X-ray detector that are arranged on a holding element so as to be movable and tiltable independently of each other.

The holding element may also be movably arranged on a base support, including an earth-vertical axis, and be arranged so as to be rotatable about the earth-vertical axis. The X-ray imaging module may be positioned for diagnostic X-ray imaging at any desired angle to a therapeutic treatment beam directed onto the patient by the radiotherapy system. A suitable rotation of the holding element about the earth-vertical axis of the base support also makes it possible for sensitive X-ray imaging components to not be located in a main radiation field of the therapy radiation during emission of the therapy beam.

In another embodiment, the base support may be securely mounted on a ceiling, a sidewall or on a floor. No restriction with respect to attachment of the base support is given thereby.

The holding element may, for example, advantageously include two longitudinal segments of equal length and a first connecting element. The longitudinal segments are vertically arranged on one end respectively of the first connecting element. The first connecting element is horizontally arranged centrally on the base support.

In yet another embodiment, the holding element may include two ring segments and a second connecting element. The two ring segments are vertically arranged on one end each of the second connecting element. The second connecting element is horizontally arranged centrally on the base support. The advantage of a holding element designed in this way is that the spacing of X-ray source and the X-ray detector from the isocenter remains constant independently of the position of the components on the holding element.

In one embodiment, the radiotherapy module may include a projecting arm, from which a therapeutic treatment beam may be directed onto a patient undergoing radiotherapy.

The projecting arm may, for example, be rotatable about an isocenter, whereby the therapeutic treatment beam may be directed onto the isocenter from different angles.

The X-ray imaging module may advantageously be rotatable about the isocenter. This provides that the diagnostic X-ray imaging is oriented onto a target region positioned in the isocenter.

BRIEF DESCRIPTION OF THE DRAWINGS

FIG. 6 shows one embodiment of a radiotherapy system with another embodiment of a holding element having two X-ray imaging modules;

FIG. 7 shows one embodiment of the radiotherapy system of FIG. 6 with a rotated holding element; and FIG. 8 shows one embodiment of the radiotherapy system of FIG. 6 with a holding element in an operating position.

DETAILED DESCRIPTION OF THE DRAWINGS

Figure 1:
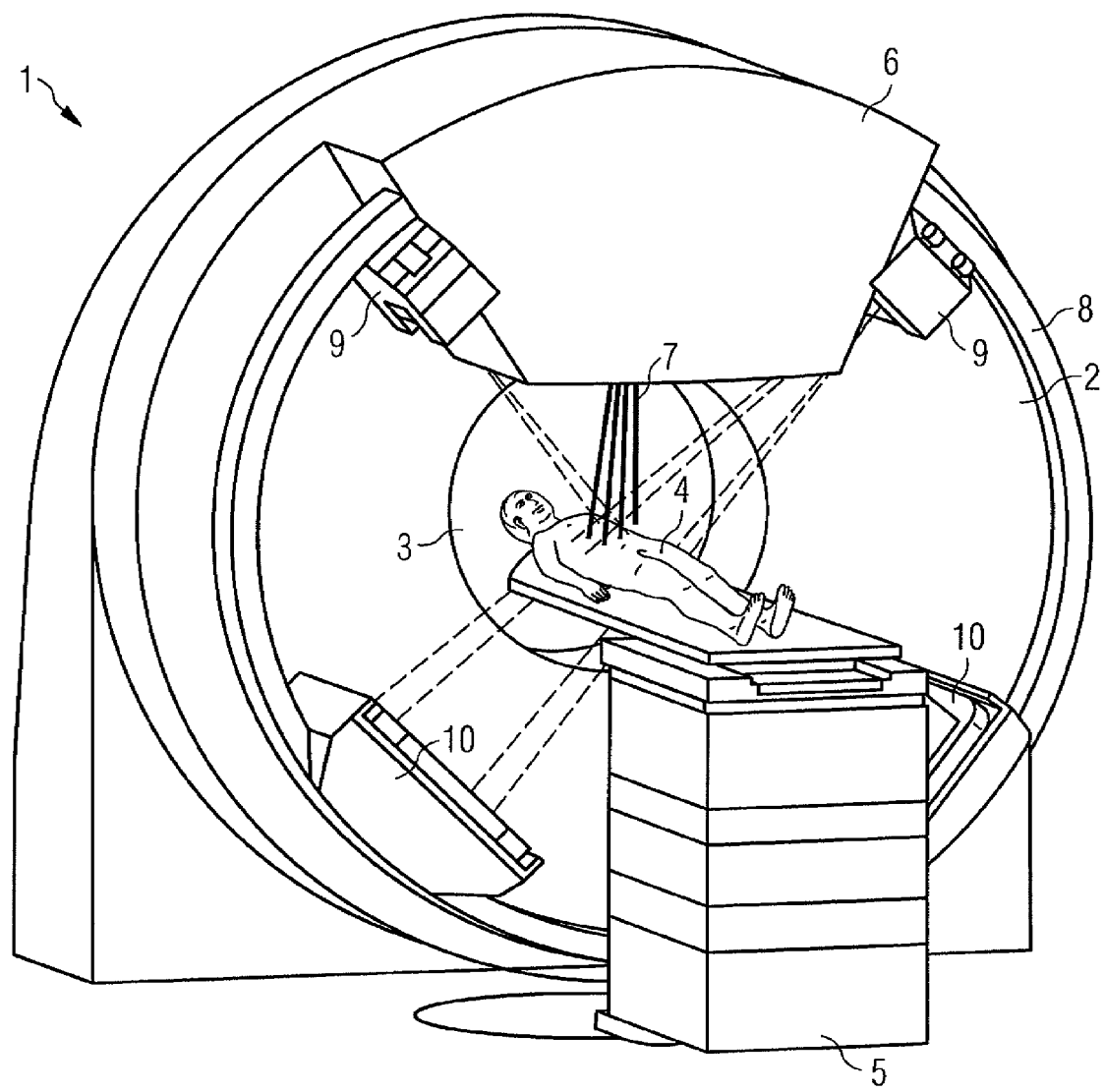
FIG. 1 shows a radiotherapy system with X-ray imaging modules according to the prior art.
Figure 2:
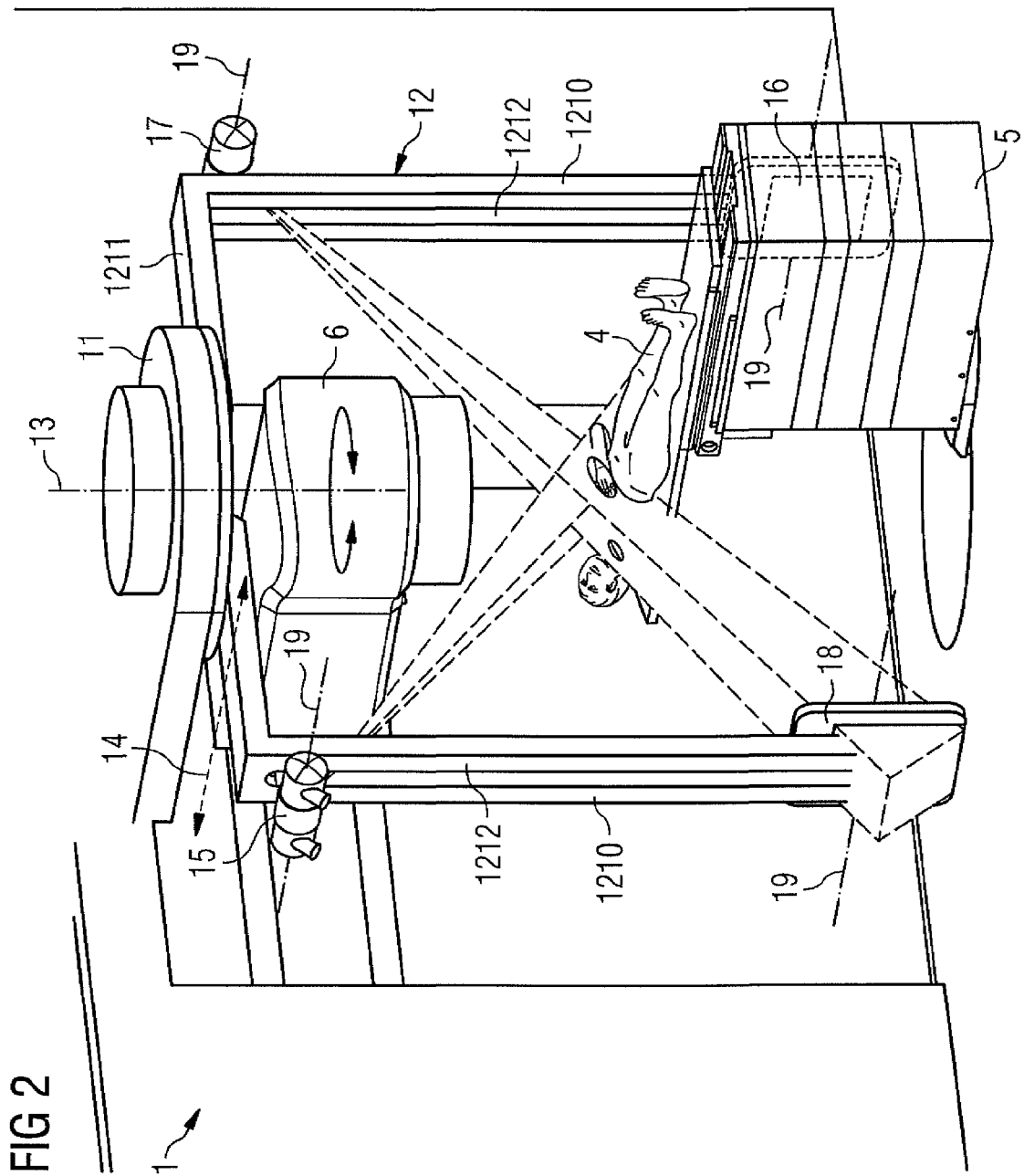
FIG. 2 shows one embodiment of a radiotherapy system with a holding element having two X-ray imaging modules.

FIG. 2 shows a radiotherapy system 1 with a holding element having two X-ray imaging modules. The radiotherapy system 1 includes a radiotherapy module with a projecting arm 6, in which a radiation source for a therapeutic treatment beam (not visible in FIG. 2) that strikes a patient 4 on a couch 5 during a treatment and a lamella collimator are at least partially located. A holding element 12 is arranged on a base support 11, which is immovably secured to a sidewall of a treatment room and includes an earth-vertical axis 13. The holding element 12 is arranged on the base support 11 so as to be movable in a direction of movement 14 and so as to be rotatable about the earth-vertical axis 13. A first X-ray imaging module, including a first X-ray source 15 and a first X-ray detector 16 (made visible in FIG. 2 by way of a partially transparent couch 5), and a second X-ray imaging module, including a second X-ray source 17 and a second X-ray detector 18, are arranged on the holding element 12. The holding element 12 includes two longitudinal segments 1210 of equal length and a first connecting element 1211. The longitudinal segments 1210 are vertically arranged on one end respectively of the first connecting element 1211. The first connecting element 1211 is horizontally arranged centrally on the base support 11. The first X-ray source 15, the second X-ray source 17, the first X-ray detector 16, and the second X-ray detector 18 (e.g., X-ray components) are arranged so as to be movable on the longitudinal elements 1210 independently of each other, and so as to be tiltable about an axis of rotation 19. The first X-ray source 15 and the first X-ray detector 16, as well as the second X-ray source 17 and the second X-ray detector 18, may be positioned so as to oppose each other and be aligned with each other by tilting about the axis of rotation 19. For example, the X-ray components 15, 18 and 16, 17 arranged on one longitudinal segment 1210 respectively may also be moved independently of each other and also be moved past each other by arranging, for example, the first X-ray source 15 and the second X-ray source 17 on the outside of the longitudinal elements 1210 and the first X-ray detector 16 and the second X-ray detector 18 on the inside of the longitudinal elements 1210. X-rays are emitted from the first X-ray source 15 and the second X-ray source 17 to the first X-ray detector 16 and the second X-ray detector 18 through a recess 1212 in the longitudinal elements 1210. For specific X-ray images, the X-ray components 15, 18 and 16, 17 arranged on each longitudinal arm 1210 may also be positioned in a plane and oriented onto the corresponding X-ray components of the other longitudinal arm 1210.

Figure 3:
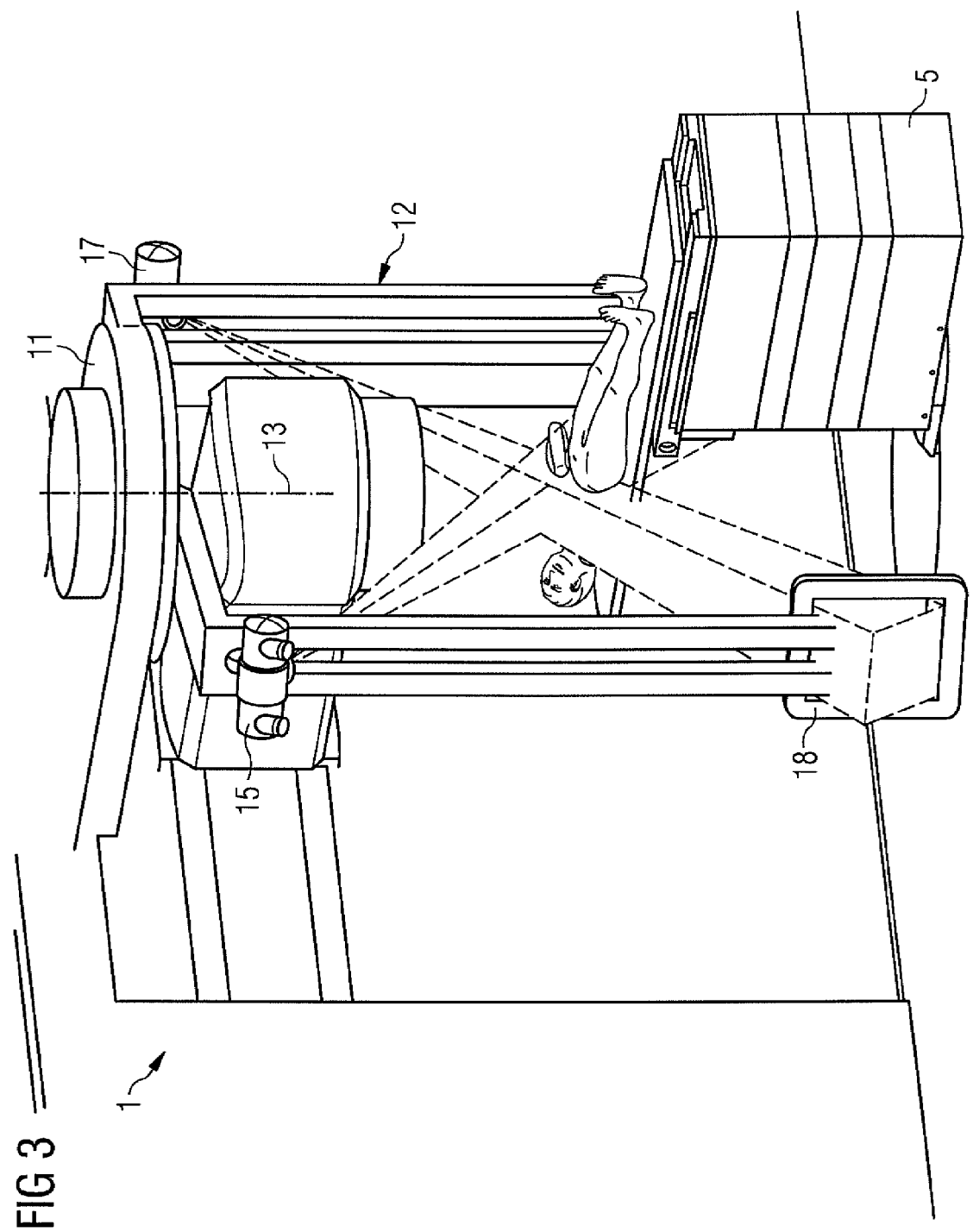
FIG. 3 shows one embodiment of the radiotherapy system of FIG. 2 with a rotated holding element.

FIG. 3 shows one embodiment of the radiotherapy system 1 shown in FIG. 2 with a rotated holding element 12. Due to the rotation of the holding element 12 about the earth-vertical axis 13 of the base support 11, the position of the X-ray imaging modules with the first X-ray source 15, the first X-ray detector 16, the second X-ray source 17 and the second X-ray detector 18 is rotated at the same time. In FIG. 3, the first X-ray detector is obscured by the couch 5. A suitable rotation of the holding element 12 about the earth-vertical axis 13 of the base support 11 also makes it possible for sensitive X-ray imaging components to not be located in a main radiation field of the therapy radiation during emission of the therapeutic treatment beam (not shown).

Figure 4:
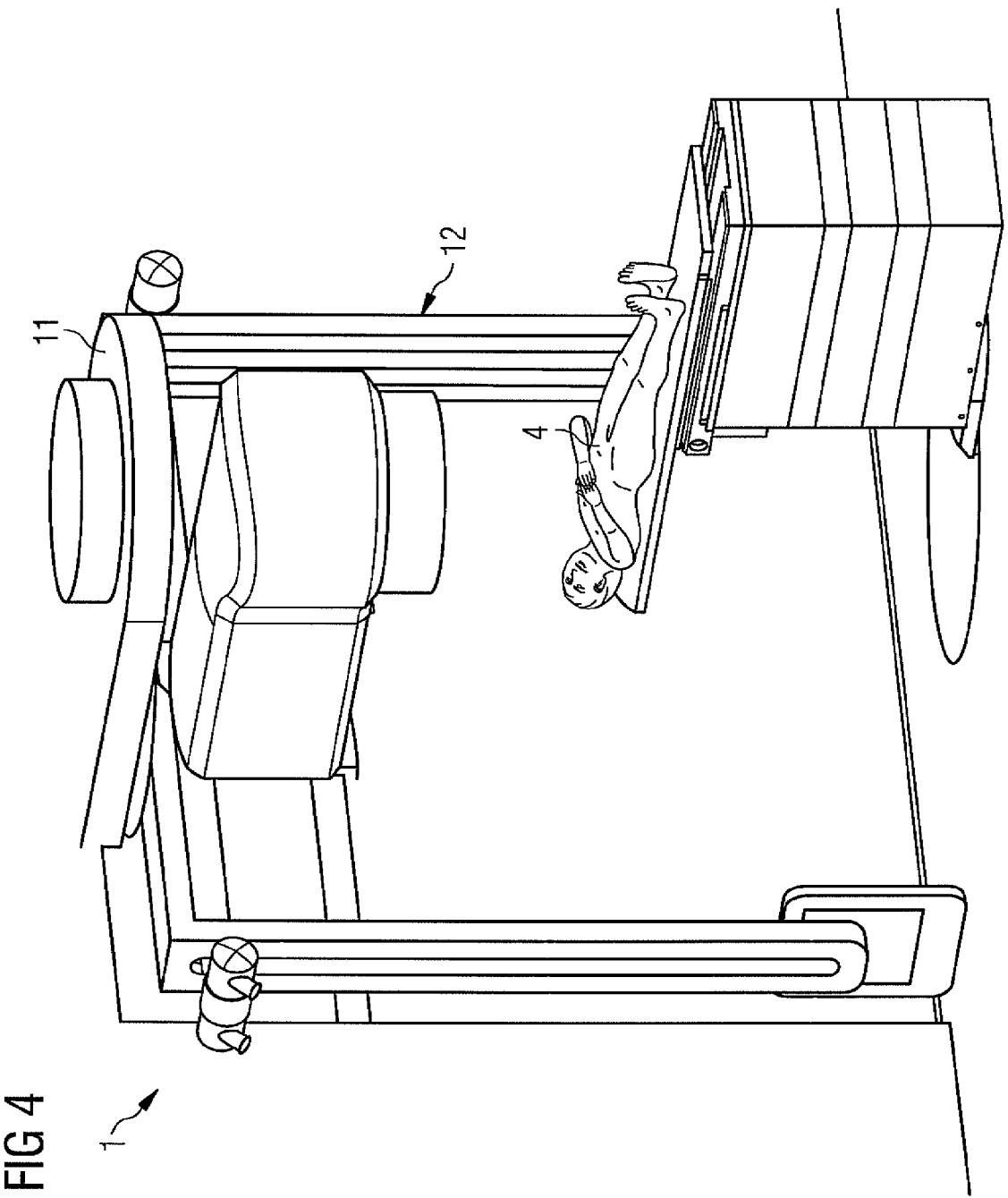
FIG. 4 shows one embodiment of the radiotherapy system of FIG. 2 with a holding element in an operating position.

FIG. 4 shows one embodiment of the radiotherapy system 1 shown in FIG. 2 with the holding element 12 in an operating position. For this purpose, the holding element 12 is moved along the base support 11. In the operating position of the holding element 12, the patient 4 may, for example, be positioned more easily for a radiotherapy session, or a user has free access to the patient 4.

Figure 5:
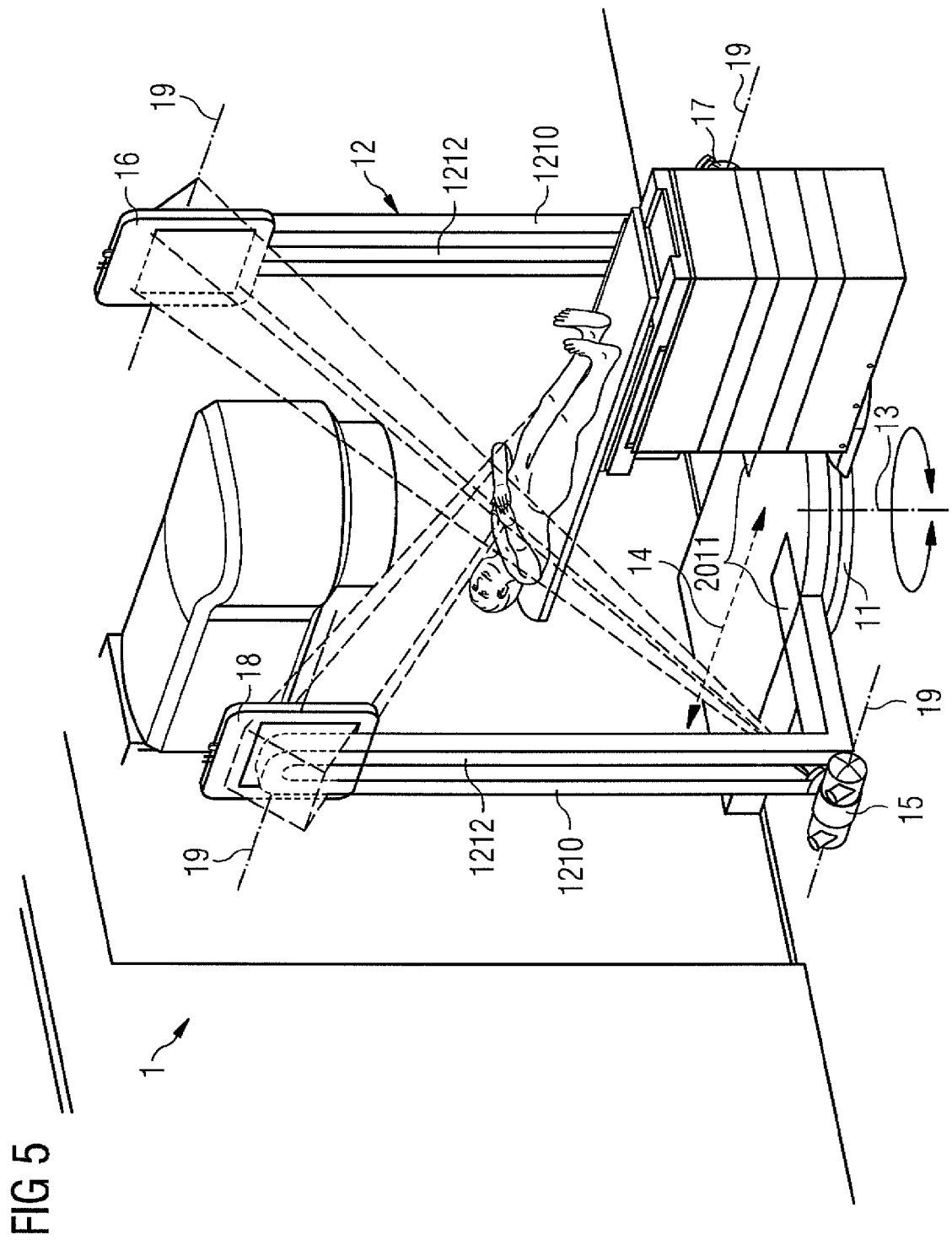
FIG. 5 shows one embodiment of a radiotherapy system with a floor-supported holding element having two X-ray imaging modules.

FIG. 5 shows one embodiment of a radiotherapy system 1 with a floor-supported holding element having two X-ray imaging modules. The radiotherapy system 1 includes a radiotherapy module as in FIG. 2. A holding element 12 is arranged on a base support 11 that is immovably secured to the floor of a treatment room. The base support 11 includes an earth-vertical axis 13. The holding element 12 is arranged on the base support 11 so as to be movable in a direction of movement 14 and so as to be rotatable about the earth-vertical axis 13. First and second X-ray imaging modules with components 15, 16, 17, 18 (e.g., a first X-ray source 15, a first X-ray detector 16, a second X-ray source 17, and a second X-ray detector 18) are arranged on the holding element 12 as in FIG. 2. The holding element 12 includes two longitudinal segments 1210 of equal length and a first connecting element 1211. The longitudinal segments 1210 are vertically arranged on one end respectively of the first connecting element 1211, and the first connecting element 1211 is horizontally arranged centrally on the base support 11. The X-ray sources 15, 17 and the X-ray detectors 16, 18 are arranged on the longitudinal elements 1210 so as to be movable independently of each other and so as to be tiltable about an axis of rotation 19. The first X-ray source 15 and the first X-ray detector 16, as well as the second X-ray source 17 and the second X-ray detector 18, may be positioned so as to oppose each other and so as to be aligned with each other by tilting about the axis of rotation 19. For example, the X-ray components 15, 18 and 16, 17 arranged on one longitudinal segment 1210 respectively may also be moved independently of each other and also past each other by arranging, for example, the X-ray sources 15, 17 on the outside of the longitudinal elements 1210 and the X-ray detectors 16, 18 on the inside of the longitudinal elements 1210. X-rays are emitted from the X-ray sources 15, 17 to the X-ray detectors 16, 18 through a recess 1212 in the longitudinal elements 1210. Rotation of the holding element 12 about the earth-vertical axis 13 of the base support 11, and movement of the holding elements 12 along the base support 11 into an operating position is also possible with this embodiment of the holding elements 12.

FIG. 6 shows a radiotherapy system with another embodiment of a holding element having two X-ray imaging modules. The radiotherapy system 1 includes a radiotherapy module as in FIG. 2. A holding element 12 is arranged on a base support 11 that is immovably secured to a sidewall of the treatment room and. The base support 11 includes an earth-vertical axis 13. The holding element 12 is arranged on the base support 11 so as to be movable in a direction of movement 14 and so as to be rotatable about the earth-vertical axis 13. First and second X-ray imaging modules with components 15, 16, 17, 18 (e.g., first X-ray source 15 and second X-ray source 17, and first X-ray detector 16 and second X-ray detector 18) are arranged on the holding element 12 as in FIG. 2. The holding element 12 includes two ring segments 1220 and a second connecting element 1221. The two ring segments 1220 are arranged on one end respectively of the second connecting element 1221. The second connecting element 1221 is horizontally arranged centrally on the base support 11. The first and second X-ray sources 15, 17 and the first and second X-ray detectors 16, 18 are arranged on the two ring segments 1220 so as to be movable independently of each other and so as to be tillable about an axis of rotation 19. The first X-ray source 15 and the first X-ray detector 16, as well as the second X-ray source 17 and the second X-ray detector 18, may be positioned so as to oppose each other and to be aligned with each other by tilting about the axis of rotation 19. For example, the X-ray components 15, 18 and 16, 17 arranged on one ring segment 1220 respectively may also be moved independently of each other and also past each other by arranging, for example, the X-ray sources 15, 17 on the outside of the ring elements 1220 and the X-ray detectors 16, 18 on the inside of the ring elements 1220. X-rays are emitted from the X-ray sources 15, 17 to the X-ray detectors 16, 18 through a recess 1212 in the ring elements 1220.

FIG. 7 shows one embodiment of the radiotherapy system 1 shown in FIG. 6 with a rotated holding element 12. Due to the rotation of the holding element 12 about the earth-vertical axis 13 of the base support 11, the position of the X-ray imaging modules with the first X-ray source 15, the first X-ray detector 16, the second X-ray source, and the second X-ray detector 18 is rotated at the same time. In FIG. 7, the second X-ray source is obscured by the couch 5.

FIG. 8 shows one embodiment of the radiotherapy system 1 shown in FIG. 6 with the holding element 12 in an operating position. For this purpose, the holding element 12 is moved along the base support 11. In the operating position of the holding element 12, a patient 4 may, for example, be positioned more easily for a radiotherapy session, or a user has free access to the patient 4.

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. A radiotherapy system comprising:
a radiotherapy module; and
at least one X-ray imaging module,
wherein the radiotherapy module and the at least one X-ray imaging module are movable independently of each other,
wherein the at least one X-ray imaging module comprises an X-ray source and an X-ray detector that are arranged on a holding element so as to be movable and tiltable independently of each other, and
wherein the holding element is arrange so as to be movable on a base support comprising an earth-vertical axis and rotatable about the earth-vertical axis.

2. The radiotherapy system as claimed in claim 1, wherein the base support is securely mounted on a ceiling, a side wall or a floor.

3. The radiotherapy system as claimed in claim 2, wherein the holding element comprises two longitudinal segments of equal length and a first connecting element,
wherein the two longitudinal segments are vertically arranged on one end respectively of the first connecting element, and
wherein the first connecting element is horizontally arranged centrally on the base support.

4. The radiotherapy system as claimed in claim 2, wherein the holding element comprises two ring segments and a second connecting element,
wherein the two ring segments are vertically arranged on one end respectively of the second connecting element, and
wherein the second connecting element is horizontally arranged centrally on the base support.

5. The radiotherapy system as claimed in claim 2, wherein the radiotherapy module comprises a projecting arm, from which a therapeutic treatment beam is directable onto a patient undergoing radiotherapy.

6. The radiotherapy system as claimed in claim 1, wherein the holding element comprises two longitudinal segments of equal length and a first connecting element,
wherein the two longitudinal segments are vertically arranged on one end respectively of the first connecting element, and
wherein the first connecting element is horizontally arranged centrally on the base support.

7. The radiotherapy system as claimed in claim 6, wherein the radiotherapy module comprises a projecting arm, from which a therapeutic treatment beam is directable onto a patient undergoing radiotherapy.

8. The radiotherapy system as claimed in claim 1, wherein the holding element comprises two ring segments and a second connecting element,
wherein the two ring segments are vertically arranged on one end respectively of the second connecting element, and
wherein the second connecting element is horizontally arranged centrally on the base support.

9. The radiotherapy system as claimed in claim 8, wherein the radiotherapy module comprises a projecting arm, from which a therapeutic treatment beam is directable onto a patient undergoing radiotherapy.

10. The radiotherapy system as claimed in claim 1, wherein the radiotherapy module comprises a projecting arm, from which a therapeutic treatment beam is directable onto a patient undergoing radiotherapy.

11. The radiotherapy system as claimed in claim 10, wherein the projecting arm is rotatable about an isocenter, and
wherein the therapeutic treatment beam is directable onto the isocenter from different angles.

12. The radiotherapy system as claimed in claim 11, wherein at least one X-ray imaging module is rotatable about the isocenter.

* * * * *